US 6,683,015 B2

(12) United States Patent
Ofori et al.

(10) Patent No.: US 6,683,015 B2
(45) Date of Patent: Jan. 27, 2004

(54) METHOD FOR REACTIVATING A CATALYST COMPOSITION

(75) Inventors: John Yaw Ofori, Niskayuna, NY (US); Peter John Bonitatebus, Jr., Guilderland, NY (US)

(73) Assignee: General Electric Company, Niskayuna, NY (US)

( * ) Notice: Subject to any disclaimer, the term of this patent is extended or adjusted under 35 U.S.C. 154(b) by 316 days.

(21) Appl. No.: 09/682,173

(22) Filed: Jul. 31, 2001

(65) Prior Publication Data

US 2003/0027709 A1 Feb. 6, 2003

(51) Int. Cl.[7] .................................................. B01J 20/34
(52) U.S. Cl. ............................. 502/29; 502/31; 502/33; 502/56
(58) Field of Search .............................. 502/27, 28, 29, 502/31, 33, 56

(56) References Cited

U.S. PATENT DOCUMENTS

| 5,981,788 | A | 11/1999 | Ofori et al. |
| 6,071,843 | A | 6/2000 | Buysch et al. |
| 6,090,737 | A | 7/2000 | Ofori |
| 6,143,937 | A | 11/2000 | Ofori |
| 6,191,060 | B1 | 2/2001 | Ofori |

OTHER PUBLICATIONS

U.S. patent application Ser. No. 09/709,805. No date.

U.S. patent application Ser. No. 09/822,129. No date.

*Primary Examiner*—Stanley S. Silverman
*Assistant Examiner*—Edward M. Johnson
(74) *Attorney, Agent, or Firm*—Andrew J. Caruso; Patrick K. Patnode

(57) ABSTRACT

The present invention is directed to a method for reactivating a deactivated carbonylation catalyst composition previously used in a carbonylation reaction involving an aromatic hydroxy compound, carbon monoxide and oxygen, so that the re-activated catalyst composition is effective at carbonylating an aromatic hydroxy compound in a subsequent oxidative carbonylation reaction.

115 Claims, No Drawings

METHOD FOR REACTIVATING A CATALYST COMPOSITION

BACKGROUND OF INVENTION

The present invention is directed to a method for reactivating a deactivated catalyst composition, and in particular to a method for reactivating a deactivated carbonylation catalyst composition, which is present in a post reaction mixture of a catalytic oxidative carbonylation reaction, and optionally recycling the re-activated catalyst composition in a subsequent oxidative carbonylation reaction without the need to individually isolate, purify, or reconstitute the original components of the catalyst composition.

A useful method for the production of aromatic carbonates includes the oxidative carbonylation of aromatic hydroxy compounds, with carbon monoxide and oxygen, which is typically catalyzed by a catalyst composition comprising a Group 8, 9 or 10 metal catalyst, various metal co-catalyst sources, a salt source, optionally an activating solvent, and optionally a base source. The lifetime of a typical carbonylation catalyst composition that can catalyze the production of aromatic carbonates, in an oxidative carbonylation reaction, is generally finite, thus resulting in a steady decrease in catalytic activity as the carbonylation reaction progresses. The decrease in catalytic activity is typically characterized by a steady decrease in the rate at which the desired aromatic carbonate is produced. Loss of catalytic activity during and after a carbonylation reaction can result from, but is not limited to, a change in reaction conditions (e.g., temperature, pressure), a decrease in the concentration of a reagent (e.g., oxygen), a change in the pH of the reaction mixture, an irreversible consumption of one or more components of the catalyst composition, and the build up of a particular side-product, which might act as a catalyst poison in the case of certain catalyst compositions.

The reactivation, and recycle, of a deactivated catalyst composition generally involves a removal step, a purification step, and a reconstitution step, wherein the individual components of the deactivated catalyst composition are first removed from a reaction mixture, purified, and then transformed into their original active forms before being recycled in a subsequent reaction. However, on a commercial scale these types of relatively complex processes are generally unattractive, because they result in the physical loss of unacceptable quantities of costly catalyst components. Consequently, a long felt yet unsatisfied need exists for a new and improved method for reactivating a deactivated catalyst composition previously used in an oxidative carbonylation reaction of an aromatic hydroxy compound, such that the re-activated catalyst composition can be re-used in a subsequent oxidative carbonylation reaction without the need to individually isolate, purify, and reconstitute the various components of the catalyst composition.

SUMMARY OF INVENTION

In one embodiment, the present invention is directed to a method for reactivating a deactivated carbonylation catalyst composition comprising a Group 8, 9 or 10 catalyst source, and a Group 14 metal first inorganic co-catalyst, which is present in a first liquid reaction mixture, said method comprising the following steps:

a first addition step, in which an aqueous solution comprising at least one protic acid source is added to said first liquid reaction mixture, forming a biphasic second liquid reaction mixture composed of an organic layer and an aqueous layer;

a mixing step, whereby the biphasic second liquid reaction mixture is effectively agitated for a predetermined amount of time, followed by a settling stage in order to repartition the mixture into the organic layer and the aqueous layer;

a first separation step, in which the organic layer of said biphasic second liquid reaction mixture is separated from said second liquid reaction mixture, to produce an aqueous third liquid reaction mixture;

an optional second separation step, in which any precipitate which was present in the denser phase of the second liquid reaction mixture is separated from the denser phase obtained after the first separation step;

an optional second addition step, in which any metal containing precipitate which was separated during the second separation step, is added to the third liquid reaction mixture to produce a fourth liquid reaction mixture; and an evaporation step, wherein the volume of said fourth liquid reaction mixture is reduced by removing a predetermined amount of at least one component by evaporation at a predetermined temperature and pressure thus producing a concentrated fourth liquid reaction mixture;

wherein the carbonylation catalyst composition contained in the concentrated fourth liquid reaction mixture is more active, than the carbonylation catalyst composition contained in said first liquid reaction mixture, at carbonylating an aromatic hydroxy compound in a subsequent oxidative carbonylation reaction.

In another embodiment, the invention is directed to a method for reactivating a deactivated carbonylation catalyst composition comprising a Group 8, 9 or 10 catalyst source and a Group 14 metal first inorganic co-catalyst, which is present in a first liquid reaction mixture, said method comprising the following steps:

an optional first evaporation step, wherein the volume of the first liquid reaction mixture is reduced by removing a predetermined amount of at least one component by evaporation at a predetermined temperature and pressure to produce a concentrated first liquid reaction mixture;

a first addition step, in which an aqueous solution comprising at least one protic acid source is added to said first liquid reaction mixture, forming a biphasic second liquid reaction mixture composed of an organic layer and an aqueous layer;

a mixing step, whereby the biphasic second liquid reaction mixture is effectively agitated for a predetermined amount of time, followed by a settling stage in order to repartition the mixture into the organic layer and the aqueous layer;

a first separation step, in which the organic layer of said second liquid reaction mixture, is separated from said second liquid reaction mixture after a predetermined amount of time, to produce an aqueous third liquid reaction mixture;

an optional second separation step, in which any precipitate which was present in the denser phase of the second liquid reaction mixture is separated from the denser phase obtained after the first separation step;

an optional second evaporation step, wherein the volume of said aqueous third liquid reaction mixture is reduced by removing a predetermined amount of at least one component by evaporation at a predetermined temperature and pressure to produce a concentrated third liquid reaction mixture;

a second addition step, wherein a solution comprising at least one member selected from the group consisting of an activating solvent, an aromatic hydroxy compound, an aromatic carbonate, and any mixtures thereof is added to the third liquid reaction mixture, forming a fourth liquid reaction mixture;

a third evaporation step, wherein the volume of the fourth liquid reaction mixture is reduced by removing a predetermined amount of at least one component by evaporation at a predetermined temperature and pressure to produce a concentrated fourth liquid reaction mixture;

a third separation step, in which any components that precipitate from the concentrated fourth liquid reaction mixture after a predetermined amount of time are separated from the concentrated fourth liquid reaction mixture, therein producing a fifth liquid reaction mixture;

an third addition step, wherein at least one member selected from the group consisting of an aromatic hydroxy compound, an organic ligand source, an aromatic carbonate, a salt source, an activating solvent, a base source, and any mixtures thereof, is added to the fifth liquid reaction mixture to produce a sixth liquid reaction mixture; and an optional fourth addition step, wherein any metal containing precipitate which was separated during the second separation step is added to the sixth liquid reaction mixture, therein producing an seventh liquid reaction mixture;

wherein the carbonylation catalyst composition contained in said seventh liquid reaction mixture is more active than the carbonylation catalyst composition contained is said first liquid reaction mixture at carbonylating an aromatic hydroxy compound in a subsequent oxidative carbonylation reaction.

In yet another embodiment, the present invention is directed to a method for reactivating a deactivated carbonylation catalyst composition comprising a Group 8, 9 or 10 catalyst source, and a Group 7 metal inorganic co-catalyst, which is present in a first liquid reaction mixture, said method comprising the following steps:

an addition step, in which an aqueous solution comprising at least one protic acid source is added to said first liquid reaction mixture, forming a biphasic second liquid reaction mixture composed of an organic layer and an aqueous layer;

a mixing step, whereby the biphasic second liquid reaction mixture is effectively agitated for a predetermined amount of time, followed by a settling stage in order to repartition the second liquid reaction mixture into the organic layer and the aqueous layer;

a separation step, in which the organic layer of said biphasic second liquid reaction mixture is separated from said second liquid reaction mixture, to produce an aqueous third liquid reaction mixture; and an evaporation step, wherein the volume of said aqueous third liquid reaction mixture is reduced by removing a predetermined amount of at least one component by evaporation at a predetermined temperature and pressure thus producing a concentrated third liquid reaction mixture;

wherein the carbonylation catalyst composition contained in the concentrated third liquid reaction mixture is more active, than the carbonylation catalyst composition contained in said first liquid reaction mixture, at carbonylating an aromatic hydroxy compound in a subsequent oxidative carbonylation reaction.

DETAILED DESCRIPTION

In one embodiment, the present invention is directed to a method for reactivating a deactivated carbonylation catalyst composition previously used in a carbonylation reaction involving an aromatic hydroxy compound, carbon monoxide and oxygen, so that the re-activated catalyst composition is effective at carbonylating an aromatic hydroxy compound in a subsequent oxidative carbonylation reaction.

The method of the present invention is suitable for a typical carbonylation catalyst composition, comprising at least a Group 8, 9, or 10 catalyst source and a Group 14 metal inorganic co-catalyst source, which when active effectively catalyzes the production of aromatic carbonates via an oxidative carbonylation of aromatic hydroxy compounds with oxygen and carbon monoxide.

In the context of the present invention, the terms "active" and "activated", when used in reference to a catalyst composition, are meant to imply a condition in which the catalyst composition can catalyze the production of a desired aromatic carbonate at a rate which is greater than, or equal to, a predetermined reference rate. Herein, the rate of an oxidative carbonylation reaction is defined in terms of the catalyst "turnover number" per hour (TON/h), which is a measure of moles of desired carbonate produced per mole of catalyst, during a predetermined amount of reaction time (e.g., one hour). For example, in one embodiment of the present invention, the catalyst TON=[(moles of diphenyl carbonate produced)/(moles of palladium)/hour]. In the context of the present invention, the term "deactivated", when used in reference to a catalyst composition, connotes a formerly "active" catalyst composition which in it's current state, produces a desired aromatic carbonate at a rate which is below a predetermined reference rate. The term "reactivated", when used in reference to a catalyst composition, is defined as the transformation of a formerly "deactivated" catalyst composition back to an "active" catalytic state, in which the catalyst composition is once again capable of catalyzing the production of a desired aromatic carbonate in a subsequent oxidative carbonylation reaction, at a rate which is greater than, or equal to, a predetermined reference rate.

In the context of the present invention, the term "reaction condition" is meant to include, but is not limited to, reactor vessel pressure, reactor vessel temperature, reaction mixture temperature, agitation rate, gas flow rates (e.g., carbon monoxide flow rate and oxygen flow rate), gas mixture composition (e.g., ratio of carbon monoxide to oxygen), the pH of the reaction mixture, the weight % of various components of the liquid reaction mixture including, but not limited to, weight % of aromatic hydroxy compound, weight % of desired carbonate, weight % of water, and weight % of activating solvent.

In the context of the present invention, the term "reaction condition" is meant to include, but is not limited to, reactor vessel pressure, reaction temperature, agitation rate, gas flow rates (e.g., carbon monoxide flow rate and oxygen flow rate), gas mixture composition (e.g., the ratio of carbon monoxide to oxygen, or the presence of an additional gas source such as nitrogen), the pH of the reaction mixture, the weight % of various components of the liquid reaction mixture including, but not limited to, the weight % of an aromatic hydroxy compound, the weight % of a desired carbonate, the weight % of water, and the weight % of activating solvent.

In the context of the present invention, the term "liquid reaction mixture" is defined as a mixture of compounds, which are present predominantly in a liquid state at ambient room temperature and pressure (e.g., about 25° C. and about 0.1 MPa). Liquid reaction mixtures can be homogeneous liquid mixtures composed of one of more phases (e.g., biphasic liquid reaction mixtures), or heterogeneous liquid-solid mixtures containing components that are present in the solid state (e.g., precipitates). In the present invention, a first liquid reaction mixture is typically a post-reaction mixture resulting from the carbonylation of an aromatic hydroxy compound using oxygen, carbon monoxide, and a catalyst composition. Herein, the individual constituents of a liquid reaction mixture are referred to as "components". The components of a typical first liquid reaction mixture include, but are not limited to, the desired aromatic carbonate, byproducts of the carbonylation reaction which include, but are not limited to, water, aryl ethers, poly-aromatic hydroxy compounds, and aromatic carbonates other than the desired aromatic carbonate, dissolved reagent gases, soluble components of the catalyst composition, insoluble components of the catalyst composition which are present as precipitates, and unreacted aromatic hydroxy compound. Suitable types of aromatic hydroxy compounds include, but are not limited to, monocyclic aromatic compounds comprising at least one hydroxy group, and polycyclic aromatic compounds comprising at least one hydroxy group. Illustrative examples of suitable aromatic hydroxy compounds include, but are not limited to, phenol, alkylphenols, alkoxyphenols, bisphenols, biphenols, and salicylic acid derivates (e.g., methyl salicylate).

The carbonylation catalyst composition present in a typical liquid reaction mixture generally comprises a catalyst, which is a first metal source selected from a Group 8, 9 or 10 metal source. Typical Group 8, 9 or 10 metal sources include ruthenium sources, rhodium sources, palladium sources, osmium sources, iridium sources, platinum sources, and mixtures thereof. In one embodiment, about 1 ppm to about 10000 ppm of a Group 8, 9, or 10 metal source is present in the catalyst composition. In another embodiment, about 1 ppm to about 1000 ppm of a the Group 8, 9, or 10 metal source is present in the catalyst composition. In yet another embodiment of the present invention, about 1 ppm to about 100 ppm of a Group 8, 9, or 10 metal source is present in the catalyst composition. A typical Group 8, 9, or 10 metal source is a palladium source, including palladium compounds. As used herein, with respect to metal sources in general, the term "compound" includes inorganic, coordination and organometallic complex compounds. The compounds are typically neutral, cationic, or anionic, depending on the charges carried by the central metal and the coordinated ligands. Other common names for these compounds include complex ions (if electrically charged), Werner complexes, and coordination complexes. The Group 8, 9, or 10 metal source is typically present in the reaction mixture in a homogeneous form that is substantially soluble in the reaction mixture, or alternatively in a heterogeneous form which is substantially insoluble in the reaction mixture, including metal sources supported on substrates and polymer bound metal sources. Examples of suitable palladium sources include, but are not limited to, palladium sponge, palladium black, palladium deposited on carbon, palladium deposited on alumina, palladium deposited on silica, palladium halides, palladium nitrates, palladium carboxylates, palladium acetates, palladium salts of β-diketones, palladium salts of β-ketoesters, and palladium compounds containing at least one of the following ligands: carbon monoxide, amine, nitrite, nitrile, isonitrile, phosphine, phosphite, phosphate, alkoxide, alkyl, aryl, silyl or olefin.

Additional metal sources which are present in the catalyst compositions are typically referred to as inorganic co-catalysts. As used herein, the term "inorganic co-catalyst" (IOCC) includes any catalyst component that contains a metal element, which is present in the catalyst composition in addition to the Group 8, 9 or 10 first metal source. Typically, one or two IOCC's are present in the catalyst composition, and thus are present in the reaction mixture as a second metal source and a third metal source, respectively. Typical IOCC's include, but are not limited to, compounds selected from the group consisting of Group 4 metal sources, Group 7 metal sources, Group 8 metal sources, Group 9 metal sources, Group 11 metal sources, Group 12 metal sources, Group 14 metal sources, Group 15 metal sources, Lanthanide sources, and mixtures thereof. Suitable forms of IOCC sources include, but are not limited to, elemental metals, metal oxides, and metal compounds in stable oxidation states. The IOCC compounds are typically neutral, cationic, or anionic, depending on the charges carried by the central atom and the coordinated ligands. The IOCC compounds are typically present in the reaction mixture in a homogeneous form that is substantially soluble in the reaction mixture, or alternatively in a heterogeneous form which is substantially insoluble in the reaction mixture, including metal sources supported on substrates and polymer bound metal sources. In one embodiment, about 1 equivalent to about 1000 equivalents of at least one IOCC source, versus the amount of a Group 8, 9, or 10 metal source, is present in the reaction mixture. In another embodiment, about 1 equivalent to about 500 equivalents of at least one IOCC source, versus the amount of a Group 8, 9, or 10 metal source, is present in the reaction mixture. In yet another embodiment of the present invention, about 1 equivalent to about 100 equivalents of at least one IOCC source, versus the amount of a Group 8, 9, or 10 metal source, is present in the reaction mixture. Examples of suitable IOCC sources for the present invention include, but are not limited to, lead sources, titanium sources, manganese sources, and copper sources. For example, in one embodiment a first IOCC is initially present in the carbonylation catalyst composition as lead(II) oxide. Other suitable lead sources include, but are not limited to, lead halide compounds (e.g., lead(II) bromide), lead alkoxy compounds (e.g., lead(II) methoxide), lead aryloxy compounds (e.g., lead(II) phenoxide), organometallic lead compounds having at least one lead-carbon bond, (e.g., alkyl lead compounds such as tetraethyllead(IV)), and lead compounds containing at least one of the following ligands: carbon monoxide, amine, nitrite, nitrile, isonitrile, cyanide, phosphine, phosphite, phosphate, alkoxide, alkyl, aryl, silyl or olefin. Mixtures of lead sources are also suitable. In another embodiment, the catalyst composition comprises a lead source in combination with a titanium source, originally charged as lead(II)oxide and titanyl(IV)oxide-bis-2,4-pentanedionate. In yet another embodiment the catalyst composition comprises a lead source in combination with a copper source, originally charged as lead(II)oxide and copper(II)-bis-2,4-pentanedionate. In yet another embodiment the catalyst composition comprises a manganese source, originally charged as manganese(II)bis-2,4-pentanedionate.

Typically, the carbonylation catalyst composition present in the liquid reaction mixture further comprises at least one salt source. Illustrative examples of suitable salt sources include, but are not limited to, alkali halides, alkaline-earth halides, guanidinium halides, and onium halides (e.g., ammonium halides, phosphonium halides, sulfonium halides), and compounds which contain an anion selected from the group consisting of carboxylates, acetates, and nitrates. Typical onium cations contain organic residues, which include C1–C6 alkyl, C6–C10 aryl, or alkyl-aryl combinations thereof. In one embodiment, about 1 equivalent to about 100000 equivalents of a salt source, versus the amount of a Group 8, 9, or 10 metal source, is present in the reaction mixture. In another embodiment, about 1 equivalent to about 10000 equivalents of a salt source, versus the amount of a Group 8, 9, or 10 metal source, is present in the reaction mixture. In yet another embodiment of the present invention, about 1 equivalent to about 5000 equivalents of a salt source, versus the amount of a Group 8, 9, or 10 metal source, is present in the reaction mixture.

When the salt source present in a carbonylation catalyst composition is an alkali halide salt source, or an alkaline-earth halide salt source, the catalyst composition typically further comprises an activating solvent. Generally, about 0.1% to about 50% by weight of activating solvent, based on the total weight of the liquid reaction mixture, is used. In another embodiment of the present invention, about 1% to about 20% by weight of activating solvent, based on the total weight of the reaction mixture is used. In yet another embodiment of the present invention, about 1% to about 10% by weight of activating solvent based on the total weight of the reaction mixture is used. For the present invention, suitable activating solvents include a polyether solvent (e.g. compounds containing two or more C—O—C linkages), and a nitrile solvent. Suitable polyether solvents include, aliphatic polyethers, and mixed aliphatic-aromatic polyethers. Examples of aliphatic polyethers include, but are not limited to, diethylene glycol dialkyl ethers such as diethylene glycol dimethyl ether (hereinafter "diglyme"), triethylene glycol dialkyl ethers such as triethylene glycol dimethyl ether (hereinafter "triglyme"), tetraethylene glycol dialkyl ethers such as tetraethylene glycol dimethyl ether (hereinafter "tetraglyme"), polyethylene glycol dialkyl ethers such as polyethylene glycol dimethyl ether and crown ethers such as 12-crown-4 (1,4,7,10-tetraoxacyclododecane), 15-crown-5 (1,4,7,10,13-pentaoxacyclopentadecane) and 18-crown-6 (1,4,7,10,13,16-hexaoxacyclooctadecane). Illustrative examples of mixed aliphatic-aromatic polyethers include, but are not limited to, diethylene glycol diphenyl ether and benzo-18-crown-6. Mixtures of polyethers are also suitable. Suitable nitrile solvents include, but are not limited to, C2–C8 aliphatic or C7–C10 aromatic mononitriles or dinitriles. Illustrative mononitriles include, but are not limited to, acetonitrile, propionitrile, and benzonitrile. Illustrative dinitriles include, but are not limited to, succinonitrile, adiponitrile, and benzodinitrile. Mixtures of nitriles are also suitable.

In another embodiment of the present invention, the carbonylation catalyst composition further comprises at least one base source. Suitable types of base sources include, but are not limited to, basic oxides, hydroxides, mono-alkoxides, poly-alkoxides, monocyclic aryloxides, polycyclic aryloxides, and tertiary amines. Illustrative examples of suitable base sources include, but are not limited to, sodium hydroxide, lithium hydroxide, potassium hydroxide, tetraalkylammonium hydroxides (e.g. tetramethylammonium hydroxide, tetraethylammonium hydroxide, methyltributylammonium hydroxide, and tetrabutylammonium hydroxide) sodium phenoxide, lithium phenoxide, potassium phenoxide, tetraalkylammonium phenoxides (e.g. tetramethylammonium phenoxide, tetraethylammonium phenoxide, methyltributylammonium phenoxide, and tetrabutylammonium phenoxide), triethyl amine, and tributyl amine. In one embodiment, about 1 equivalent to about 10000 equivalents of a base source, versus the amount of a Group 8, 9, or 10 metal source, is present in the reaction mixture. In another embodiment, about 1 equivalent to about 1000 equivalents of a base source, versus the amount of a Group 8, 9, or 10 metal source, is present in the reaction mixture. In yet another embodiment of the present invention, about 1 equivalent to about 500 equivalents of a base source, versus the amount of a Group 8, 9, or 10 metal source, is present in the reaction mixture.

In the context of the present invention, the term "evaporation" is defined as the conversion of a component from the liquid state to the vapor state. The evaporation steps in the present method are included to reduce the volume of a particular liquid reaction mixture by concentrating that particular liquid reaction mixture by removing at least one volatile component, at a predetermined temperature and pressure, such as an aromatic hydroxy compound, a halogenated aromatic hydroxy compound, a hydrohalogenic acid, an activating solvent, or water, from a particular liquid reaction mixture. For example, in one embodiment, the initial step in the method is an optional evaporation step, which is included to reduce the volume of the first liquid reaction mixture.

One element of the present invention involves the addition of an "aqueous solution" comprising at least one "protic acid source" to a first liquid reaction mixture. Herein, the term "aqueous solution" includes those solutions where water is present as a solvent. A "protic acid source" is defined as a chemical species that can act as a source of protons (e.g., a Brönsted acid). Suitable examples of protic acid sources includes, but are not limited to, hydrohalogenic acids (e.g., hydrobromic acid, hydrochloric acid, and hydroiodic acid), sulfuric acid, nitric acid, and carboxylic acids. In one embodiment of the present invention, the aqueous solution consists of an aqueous hydrobromic acid solution where the hydrobromic acid is present at about 1 weight % (wt %) to about 48 wt %, based on the total weight of the solution. In another embodiment, the aqueous solution consists of an aqueous hydrobromic acid solution where the hydrobromic acid is present at about 11 wt % to about 20 wt %, based on the total weight of the solution. In yet another embodiment, the aqueous solution consists of an aqueous hydrobromic acid solution where the hydrobromic acid is present at about 1 wt % to about 10 wt %, based on the total weight of the solution. Addition of the aqueous solution to a primarily organic first liquid reaction mixture produces a biphasic second liquid reaction mixture with an organic phase and an aqueous phase, and can cause the formation of a lead containing precipitate, especially at lower concentrations of hydrobromic acid (e.g., about 3 weight %). The addition can be performed using equipment known to those skilled in the art including, but not limited to, a solvent extraction column, a mixer-settler vessel, and combinations thereof. Suitable temperatures for the addition are between about 60° C. and about 140° C. In one embodiment, the temperature of the addition is about 85° C. Upon addition of the aqueous solution to the first liquid reaction mixture, the metal containing components, the salt source, and the cationic component of base source present in the catalyst composition will typically migrate from the organic phase to the aqueous phase. Depending on the components of a particular catalyst composition, a mixing step can be repeated multiple times in order to maximize the extraction of the water-soluble components of the carbonylation catalyst composition from the organic phase into the aqueous phase. Stirring, agitating, shaking, or inverting the biphasic second liquid reaction mixture can be used to obtain suitable mixing of the organic and aqueous phases. Effective phase separation of the second liquid reaction mixture is influenced by the temperature of the liquid reaction mixture, which is selected based on the specific composition of the liquid reaction mixture. Suitable temperatures for the phase separation of the second liquid reaction mixture are between about 60° C. and about 140° C. In one embodiment, the temperature of the second liquid reaction mixture during phase separation is about 85° C.

Once effective phase separation has occurred, precipitate that may be present in the biphasic second liquid reaction mixture is typically separated in a first separation step. In the context of the present invention, the term "separation" is defined as the isolation of at least one component of a liquid reaction mixture from the remaining components of the liquid reaction mixture. Herein, decanting, filtering, centrifuging, evaporating, or any combinations thereof can be used to achieve effective separation of a given component from a liquid reaction mixture. In the context of the present invention, the term separation also includes the division of the biphasic liquid reaction mixture into a separate organic phase liquid reaction mixture, and an aqueous phase liquid reaction mixture. When hydrobromic acid is the protic acid source in the aqueous solution that is added to the first liquid reaction mixture in the first addition step, typically a lead containing precipitate will form as a result of a reaction between the bromide ion and the lead source, leading to lead compounds such as lead(II) bromide which typically have low solubility constants (e.g., $K_{sp}$) in aqueous and organic solutions. The lead containing precipitate that is separated in this first separation step is typically combined with the other components of the catalyst composition at a later point in the method.

In one embodiment, an evaporation step is performed on the fourth liquid reaction mixture in order to reduce its volume, by removing a predetermined amount of water, to produce a concentrated fourth liquid reaction mixture which can either be returned to a subsequent carbonylation reaction to effectively catalyze the carbonylation or an aromatic hydroxy compound, or in an alternative embodiment, can be subjected to further steps before being returned to a subsequent carbonylation reaction. In one embodiment, a second addition step is made to the concentrated fourth liquid reaction mixture, in which a solution comprising an activating solvent is added to the fourth liquid reaction mixture to yield a fifth liquid reaction mixture. The fifth liquid reaction mixture is then subjected to a further evaporation step in order to reduce its volume by removing at least one volatile component. This evaporation step is followed by a third addition step, where additional components, such as a base source, are added to the fifth liquid reaction mixture to yield a sixth liquid reaction mixture. Typically the sixth liquid reaction mixture will contain a precipitate, which is removed by filtration, to produce a seventh liquid reaction mixture. Finally, the precipitate which was separated from the second liquid reaction mixture in a prior separation step, is combined along with the seventh liquid reaction mixture, thus forming an eighth liquid reaction mixture which comprises the reactivated catalyst composition which can to be returned to a subsequent carbonylation reaction to effectively catalyze the carbonylation or an aromatic hydroxy compound.

The following prophetic example is included to provide additional guidance to those skilled in the art at practicing the claimed invention. The prophetic example provided describes the manner by which one embodiment of the present method could be practiced by a person skilled in the art. Accordingly, the following prophetic example is not intended to limit the invention, as defined in the appended claims, in any manner.

PROPHETIC EXAMPLE 1

A first liquid reaction mixture, which originates from a first carbonylation reaction in which phenol is carbonylated to diphenyl carbonate at an palladium turnover rate which is greater than about 1000 palladium turnovers/hour (TON/hr)) with a catalyst composition comprising about 15 ppm palladium, about 56 equivalents lead vs. palladium, about 2 equivalents titanium vs. palladium, about 400 equivalents of sodium bromide vs palladium, about 120 equivalents of sodium hydroxide vs palladium, and about 7 weight % of tetraglyme, should be heated to about 85° C. An equal volume of an aqueous solution of about 15% hydrobromic acid is added to the first liquid reaction mixture at about 85° C. to produce a biphasic second liquid reaction mixture. The resulting biphasic second liquid mixture is agitated for about 5 minutes with vigorous stirring, and then allowed to phase separate at about 85° C. and about 0.1 MPa. Upon cooling, the organic phase is removed from the second liquid reaction mixture, leaving behind an aqueous third liquid reaction mixture. At this point, if any precipitate is present in the denser phase of the biphasic second liquid reaction mixture, the denser phase of the biphasic second liquid reaction mixture is filtered to remove the precipitate, and the precipitate is retained. A sufficient amount of tetraglyme is added to the aqueous third liquid reaction mixture to produce a fourth liquid reaction mixture that is about 7 weight % tetraglyme. The fourth liquid mixture is heated to about 60° C. at a pressure between about 0.001 MPa and about 0.004 MPa, to remove volatile components, including water, by evaporation until the volume of the fourth liquid reaction mixture is reduced by about 95%, which ultimately produces a concentrated fourth liquid reaction mixture. The concentrated fourth liquid reaction mixture is filtered to remove any precipitates, to produce a fifth liquid reaction mixture. A sufficient amount of NaOH is added to the fifth liquid reaction mixture to produce a sixth liquid reaction mixture in which about 120 equivalents of sodium hydroxide vs palladium are present. Any precipitate previously separated from the denser phase of the second liquid reaction mixture is added to the sixth liquid reaction mixture, thus forming a seventh liquid reaction mixture. The seventh liquid reaction mixture now contains the reactivated catalyst composition, and can be resubmitted into a second carbonylation reaction. If the second carbonylation reaction is carried out under similar operating conditions as the first carbonylation reaction (e.g., about 100° C. under a pressure of about 9 MPa of a premixed gas composition comprising about 8% oxygen in carbon monoxide with vigorous stirring), diphenyl carbonate will be produced at a palladium turnover rate which is comparable to the palladium turnover rate which was originally observed in the first carbonylation reaction.

While the invention has been illustrated and described, it is not intended to be limited to the details shown, since various modifications and substitutions can be made without departing in any way from the spirit of the present invention. As such, further modifications and equivalents of the invention herein disclosed can occur to persons skilled in the art using no more than routine experimentation, and all such modifications and equivalents are believed to be within the spirit and scope of the invention as defined by the following claims.

What is claimed is:

1. A method for reactivating a deactivated carbonylation catalyst composition comprising a Group 8, 9 or 10 catalyst source, and a Group 14 metal first inorganic co-catalyst, which is present in a first liquid reaction mixture, said method comprising the following steps:

a first addition step, in which an aqueous solution comprising at least one protic acid source is added to said first liquid reaction mixture, forming a biphasic second liquid reaction mixture composed of an organic layer and an aqueous layer;

a mixing step, whereby the biphasic second liquid reaction mixture is effectively agitated for a predetermined amount of time, followed by a settling stage in order to re-partition the mixture into the organic layer and the aqueous layer;

a first separation step, in which the organic layer of said biphasic second liquid reaction mixture is separated from said second liquid reaction mixture, to produce an aqueous third liquid reaction mixture;

an optional second separation step, in which any precipitate which was present in the denser phase of the second liquid reaction mixture is separated from the denser phase obtained after the first separation step;

an optional second addition step, in which any metal containing precipitate which was separated during the second separation step, is added to the third liquid reaction mixture to produce a fourth liquid reaction mixture; and an evaporation step, wherein the volume of said fourth liquid reaction mixture is reduced by removing a predetermined amount of at least one component by evaporation at a predetermined temperature and pressure thus producing a concentrated fourth liquid reaction mixture;

wherein the carbonylation catalyst composition contained in the concentrated fourth liquid reaction mixture is more active, than the carbonylation catalyst composition contained in said first liquid reaction mixture, at carbonylating an aromatic hydroxy compound in a subsequent oxidative carbonylation reaction.

2. The method of claim 1, wherein the Group 8, 9 or 10 metal source is a palladium source.

3. The method of claim 2, wherein the Group 14 metal source is a lead source.

4. The method of claim 3, wherein the palladium source is present in an amount which is between about 1 ppm and 10000 ppm, and the lead source is present in an amount which is between about 1 equivalent and about 1000 equivalents versus the amount of palladium present.

5. The method of claim 1, wherein the carbonylation catalyst composition further comprises a second inorganic co-catalyst source which is a member selected from the group consisting of a Group 4 metal source, and a Group 11 metal source.

6. The method of claim 5, wherein the second inorganic co-catalyst source is at least one member selected from the group consisting of a titanium source, and a copper source.

7. The method of claim 6, wherein the second inorganic co-catalyst is present in an amount which is between about 1 equivalent and about 1000 equivalents versus the amount of Group 8, 9 or 10 metal source present.

8. The method of claim 1, wherein the carbonylation catalyst composition further comprises a salt source.

9. The method of claim 8, wherein the salt source is at least one member selected from the group consisting of an alkali halide, an alkaline-earth halide, a guanidinium halide, an ammonium halide, a phosphonium halide, a sulfonium halide, a carboxylate, an acetate, and a nitrate.

10. The method of claim 8, wherein the salt source is at least one member selected from the group consisting of lithium bromide, sodium bromide, potassium bromide, calcium bromide, magnesium bromide, tetrabutylammonium bromide, tetraethylammonium bromide, tetramethylammonium bromide, hexaethylguanidinium bromide, lithium chloride, sodium chloride, potassium chloride, calcium chloride, magnesium chloride, tetrabutylammonium chloride, tetraethylammonium chloride, tetramethylammonium chloride, hexaethylguanidinium chloride, sodium acetate, and sodium nitrate.

11. The method of claim 8, wherein the salt source is present in an amount which is between about 1 equivalent and about 100000 equivalents versus the amount of Group 8, 9 or 10 metal source present.

12. The method of claim 1, wherein the carbonylation catalyst composition further comprises at least one activating solvent.

13. The method of claim 12, wherein the activating solvent is at least one member selected from the group consisting of a polyether, a nitrile, and mixtures thereof.

14. The method of claim 13, wherein the activating solvent is present in an amount which between about 0.1 weight % and about 50 weight % based on the total weight of the first liquid reaction mixture.

15. The method of claim 1, wherein the carbonylation catalyst composition further comprises at least one base source.

16. The method of claim 15, wherein the base source is at least one member selected from the group consisting of a basic oxide, a hydroxide, a monoalkoxide, a poly-alkoxide, a monocyclic aryloxide, a polycyclic aryloxide, and a tertiary amine.

17. The method of claim 15, wherein the base source is at least one member selected from the group consisting of sodium hydroxide, lithium hydroxide, potassium hydroxide, tetramethylammonium hydroxide, tetraethylammonium hydroxide, methyltributylammonium hydroxide, tetrabutylammonium hydroxide, sodium phenoxide, lithium phenoxide, potassium phenoxide, tetramethylammonium phenoxide, tetraethylammonium phenoxide, methyltributylammonium phenoxide, tetrabutylammonium phenoxide, triethyl amine, tributyl amine, and any mixtures thereof.

18. The method of claim 15, wherein the base source is present in an amount which is between about 1 equivalent and about 1000 equivalents versus the amount of Group 8, 9 or 10 metal source present.

19. The method of claim 1, wherein the first liquid reaction mixture comprises at least one member selected from the group consisting of an aromatic carbonate, an aromatic hydroxy compound, a poly-aromatic hydroxy compound, a halogenated aromatic hydroxy compound, water, an aryl ether, and any mixtures thereof.

20. The method of claim 1, wherein the protic acid source is at least one member selected from the group consisting of hydrobromic acid, hydrochloric acid, sulfuric acid, nitric acid, acetic acid, and any mixtures thereof.

21. The method of claim 20, wherein the amount of protic acid source present in the aqueous solution is between about 1 weight % and about 48 weight % based on the total weight of the aqueous solution.

22. The method of claim 21, wherein the addition of the aqueous solution is made by using at least one aliquot of an aqueous solution, wherein the amount of protic acid source present in each individual aliquot is different, and wherein the resulting second liquid reaction mixture contains two phases after all the aliquots have been added and after agitation and settling are complete, and wherein the total volume of the aqueous solution added to the first liquid reaction mixture is between about 1% and about 200% of the volume of the first liquid reaction mixture.

23. The method of claim 22, wherein the extraction time, which includes the agitation and settling time, after the addition of each aliquot is between about 0.1 minutes and 120 minutes, and the temperature of the liquid reaction mixture after the addition of each aliquot is between about 60° C. and about 140° C. during the extraction.

24. The method of claim 23, wherein the addition of the aqueous solution to the first liquid reaction mixture, the mixing step, and first separation step where the organic layer is separated from the second liquid reaction mixture, are performed by using an extraction column, or a mixer followed by an extraction column.

25. The method of claim 1, wherein the addition of the aqueous solution to the first liquid reaction mixture, the mixing step, and the first separation step, are made using a mixer-settler vessel.

26. The method of claim 1, wherein the precipitate separated in the second separation step comprises a Group 14 metal source.

27. The method of claim 26, wherein the Group 14 metal source is a lead source.

28. The method of claim 1, wherein the separation of the aqueous layer from the second liquid reaction mixture is by decanting.

29. The method of claim 1, wherein the third liquid reaction mixture comprises at least one component of the catalyst composition.

30. The method of claim 1, wherein the volume of the fourth liquid reaction mixture is reduced by up to about 95% by evaporation in the evaporation step.

31. The method of claim 1, wherein the fourth liquid reaction mixture is evaporated up to almost dryness in the evaporation step.

32. The method of claim 1, wherein the temperature of fourth liquid reaction mixture during the evaporation step is between about 25° C. and about 220° C., and the pressure during the evaporation step is between about $1.3 \times 10^{-4}$ MPa and about 10 MPa.

33. The method of claim 1, wherein the temperature of the second liquid reaction mixture during the first separation step is about 85° C.

34. A method for reactivating a deactivated carbonylation catalyst composition comprising a Group 8, 9 or 10 catalyst source and a Group 14 metal first inorganic co-catalyst, which is present in a first liquid reaction mixture, said method comprising the following steps:

an optional first evaporation step, wherein the volume of the first liquid reaction mixture is reduced by removing a predetermined amount of at least one component by evaporation at a predetermined temperature and pressure to produce a concentrated first liquid reaction mixture;

a first addition step, in which an aqueous solution comprising at least one protic acid source is added to said first liquid reaction mixture, forming a biphasic second liquid reaction mixture composed of an organic layer and an aqueous layer;

a mixing step, whereby the biphasic second liquid reaction mixture is effectively agitated for a predetermined amount of time, followed by a settling stage in order to repartition the mixture into the organic layer and the aqueous layer;

a first separation step, in which the organic layer of said second liquid reaction mixture, is separated from said second liquid reaction mixture after a predetermined amount of time, to produce an aqueous third liquid reaction mixture;

an optional second separation step, in which any precipitate which was present in the denser phase of the second liquid reaction mixture is separated from the denser phase obtained after the first separation step;

an optional second evaporation step, wherein the volume of said aqueous third liquid reaction mixture is reduced by removing a predetermined amount of at least one component by evaporation at a predetermined temperature and pressure to produce a concentrated third liquid reaction mixture;

a second addition step, wherein a solution comprising at least one member selected from the group consisting of an activating solvent, an aromatic hydroxy compound, an aromatic carbonate, and any mixtures thereof is added to the third liquid reaction mixture, forming a fourth liquid reaction mixture;

a third evaporation step, wherein the volume of the fourth liquid reaction mixture is reduced by removing a predetermined amount of at least one component by evaporation at a predetermined temperature and pressure to produce a concentrated fourth liquid reaction mixture;

a third separation step, in which any components that precipitate from the concentrated fourth liquid reaction mixture after a predetermined amount of time are separated from the concentrated fourth liquid reaction mixture, therein producing a fifth liquid reaction mixture;

an third addition step, wherein at least one member selected from the group consisting of an aromatic hydroxy compound, an organic ligand source, an aromatic carbonate, a salt source, an activating solvent, a base source, and any mixtures thereof, is added to the fifth liquid reaction mixture to produce a sixth liquid reaction mixture; and an optional fourth addition step, wherein any metal containing precipitate which was separated during the second separation step is added to the sixth liquid reaction mixture, therein producing an seventh liquid reaction mixture;

wherein the carbonylation catalyst composition contained in said seventh liquid reaction mixture is more active than the carbonylation catalyst composition contained is said first liquid reaction mixture at carbonylating an aromatic hydroxy compound in a subsequent oxidative carbonylation reaction.

35. The method of claim 34, wherein the Group 8, 9 or 10 metal source is a palladium source.

36. The method of claim 35, wherein the Group 14 metal inorganic co-catalyst source is a lead source.

37. The method of claim 36, wherein the palladium source is present in an amount which is between about 1 ppm and 10000 ppm, and the lead source is present in an amount which is between about 1 equivalent and about 1000 equivalents versus the amount of palladium present.

38. The method of claim 34, wherein the carbonylation catalyst composition further comprises a second inorganic co-catalyst source which is a member selected from the group consisting of a Group 4 metal source, and a Group 11 metal source.

39. The method of claim 38, wherein the second inorganic co-catalyst source is at least one member selected from the group consisting of a titanium source, and a copper source.

40. The method of claim 39, wherein the inorganic co-catalyst is present in an amount which is between about 1 equivalent and about 1000 equivalents versus the amount of Group 8, 9 or 10 metal source present.

41. The method of claim 34, wherein the carbonylation catalyst composition further comprises a salt source.

42. The method of claim 41, wherein the salt source is at least one member selected from the group consisting of an alkali halide, an alkaline-earth halide, a guanidinium halide, an ammonium halide, a phosphonium halide, a sulfonium halide, a carboxylate, an acetate, a benzoate, and a nitrate.

43. The method of claim 41, wherein the salt source is at least one member selected from the group consisting of lithium bromide, sodium bromide, potassium bromide, calcium bromide, magnesium bromide, tetrabutylammonium bromide, tetraethylammonium bromide, tetramethylammonium bromide, hexaethylguanidinium bromide, lithium chloride, sodium chloride, potassium chloride, calcium chloride, magnesium chloride, tetrabutylammonium chloride, tetraethylammonium chloride, tetramethylammonium chloride, hexaethylguanidinium chloride, sodium acetate, and sodium nitrate.

44. The method of claim 41, wherein the salt source is present in an amount which is between about 1 equivalent and about 100000 equivalents versus the amount of Group 8, 9 or 10 metal source present.

45. The method of claim 34, wherein the carbonylation catalyst composition further comprises at least one activating solvent.

46. The method of claim 45, wherein the activating solvent is at least one member selected from the group consisting of a polyether, a nitrile, and any mixtures thereof.

47. The method of claim 46, wherein the activating solvent is present in an amount which is between about 0.1 weight % and about 50 weight % based on the total volume of the first liquid reaction mixture.

48. The method of claim 34, wherein the carbonylation catalyst composition further comprises at least one base source.

49. The method of claim 48, wherein the base source is at least one member selected from the group consisting of a basic oxide, a hydroxide, a monoalkoxide, a poly-alkoxide, a monocyclic aryloxide, a polycyclic aryloxide, and a tertiary amine.

50. The method of claim 48, wherein the base source is at least one member selected from the group consisting of sodium hydroxide, lithium hydroxide, potassium hydroxide, tetramethylammonium hydroxide, tetraethylammonium hydroxide, methyltributylammonium hydroxide, tetrabutylammonium hydroxide, sodium phenoxide, lithium phenoxide, potassium phenoxide, tetramethylammonium phenoxide, tetraethylammonium phenoxide, methyltributylammonium phenoxide, tetrabutylammonium phenoxide, triethyl amine, tributyl amine, and any mixtures thereof.

51. The method of claim 48, wherein the base source is present in an amount which is between about 1 equivalent and about 1000 equivalents versus the amount of Group 8, 9 or 10 metal source present.

52. The method of claim 34, wherein the first liquid reaction mixture comprises at least one member selected from the group consisting of an aromatic carbonate, an aromatic hydroxy compound, a poly-aromatic hydroxy compound, a halogenated aromatic hydroxy compound, water, an aryl ether, and any mixtures thereof.

53. The method of claim of 34, wherein an aromatic hydroxy compound is removed from the first reaction mixture in the first evaporation step.

54. The method of claim 53, wherein the aromatic hydroxy compound is at least one member selected from the group consisting of phenol, 2-bromophenol, and 4-bromophenol.

55. The method of claim 54, wherein the amount of aromatic hydroxy compound removed from the first reaction mixture in the first evaporation step is between about 1 weight % and 75 weight % based on the total weight of the first reaction mixture.

56. The method of claim 34, wherein the temperature of first liquid reaction mixture during the first evaporation step is between about 25° C. and about 220° C., and the pressure of during the first evaporation step is between about $1.3 \times 10^{-4}$ MPa and about 10 MPa.

57. The method of claim 34, wherein the protic acid source is at least one member selected from the group consisting of hydrobromic acid, hydrochloric acid, sulfuric acid, nitric acid, and acetic acid.

58. The method of claim 57, wherein the amount of protic acid source present in the aqueous solution is between about 1 weight % and about 48 weight % based on the total weight of the aqueous solution.

59. The method of claim 58, wherein the addition of the aqueous solution is made by using at least one aliquot of an aqueous solution, wherein the amount of protic acid source present in each individual aliquot is different, and wherein the resulting second liquid reaction mixture contains two phases after all the aliquots have been added, and wherein the total volume of the aqueous solution added to the first liquid reaction mixture is between about 1% and about 200% of the volume of the first liquid reaction mixture.

60. The method of claim 59, wherein the extraction time after the addition of each aliquot is between about 0.1 minutes and 120 minutes, and the temperature of the liquid reaction mixture after the addition of each aliquot is between about 60° C. and about 140° C.

61. The method of claim 60, wherein the addition of the aqueous solution to the first liquid reaction mixture, the mixing step, and first separation step where the organic layer is separated from the second liquid reaction mixture, are performed by using an extraction column, or a mixer followed by an extraction column, or a mixer-settler.

62. The method of claim 34, wherein the biphasic second liquid reaction mixture is agitated by stirring.

63. The method of claim 34, wherein the precipitate separated in the first separation step comprises a Group 14 metal source.

64. The method of claim 63, wherein the Group 14 metal source is a lead source.

65. The method of claim 34, wherein the separation of the organic layer from the second liquid reaction mixture in the first separation step is by decanting.

66. The method of claim 34, wherein the aqueous third liquid reaction mixture comprises at least one component of the catalyst composition.

67. The method of claim 34, wherein at least one members selected from the group consisting of water, a protic acid source, an aromatic hydroxy compound, and an activating solvent is removed from the third liquid reaction mixture in the second evaporation step.

68. The method of claim of 67, wherein the volume of the aqueous third liquid reaction mixture is reduced by up to about 99% by evaporation.

69. The method of claim 34, wherein the aqueous third liquid reaction mixture is evaporated almost up to dryness.

70. The method of claim 34, wherein the temperature of the aqueous third liquid reaction mixture during the second evaporation step is between about 25° C. and about 220° C., and the pressure of during the second evaporation step is between about $1.3 \times 10^{-4}$ MPa and about 10 MPa.

71. The method of claim 34, wherein the activating solvent added during the second addition step is at least one member selected from the group consisting of a polyether, and a nitrile.

72. The method of claim 34, wherein the solution added during the second addition step further comprises an aromatic hydroxy compound.

73. The method of claim 72, wherein the aromatic hydroxy compound is phenol.

74. The method of claim of 34, wherein the component removed from the fourth liquid reaction mixture in the third evaporation step is water.

75. The method of claim 74, wherein the amount of later removed is between about 1 weight % and about 99 weight % based on the total weight of the fourth liquid reaction mixture.

76. The method of claim 34, wherein the temperature of fourth liquid reaction mixture during the third evaporation step is between about 25° C. and about 220° C., and the pressure of during the third evaporation step is between about $1.3 \times 10^{-4}$ MPa and about 10 MPa.

77. The method of claim 34, wherein the aromatic hydroxy compound added in the third addition step is phenol.

78. The method of claim 34, wherein the ligand source added in the third addition step is 2,4-pentanedionate.

79. The method of claim 34, wherein the base source added in the third addition step is sodium hydroxide.

80. The method of claim 34, wherein the precipitate removed in the third separation step is removed by filtration or centrifugation.

81. The method of claim 80, wherein the precipitate removed in the third separation step is a salt source.

82. The method of claim 81, wherein the salt source is an alkali halide source or an alkaline-earth halide source.

83. The method of claim 81, wherein the salt source is at least one member selected from the group consisting of lithium bromide, sodium bromide, potassium bromide, calcium bromide, magnesium bromide, lithium chloride, sodium chloride, potassium chloride, calcium chloride, and magnesium chloride.

84. The method of claim 34, wherein the temperature of the second liquid reaction mixture during the first separation step is about 85° C.

85. A method for reactivating a deactivated catalyst composition used in an oxidative carbonylation reaction of phenol to produce diphenyl carbonate using carbon monoxide and oxygen, said catalyst composition comprising a palladium source, a lead source, sodium bromide and a polyether solvent, contained in a first liquid reaction mixture further comprising phenol, diphenyl carbonate, and water, said method comprising the following steps:

a first addition step, in which an aqueous solution comprising hydrobromic acid is added to said first liquid reaction mixture, forming a biphasic second liquid reaction mixture composed of an organic layer and an aqueous layer;

a mixing step, whereby the biphasic second liquid reaction mixture is effectively agitated for a predetermined amount of time, followed by a settling stage in order to re-partition the mixture into the organic layer and the aqueous layer;

a first separation step, in which the aqueous layer of said biphasic second liquid reaction mixture is separated from said second liquid reaction mixture, to produce an aqueous third liquid reaction mixture;

an optional second separation step, in which any precipitate which was present in the denser phase of the second liquid reaction mixture is separated from the denser phase obtained after the first separation step;

an optional second addition step, in which any metal containing precipitate which was separated during the second separation step, is added to the third liquid reaction mixture to produce a fourth liquid reaction mixture; and an evaporation step, wherein the volume of said fourth liquid reaction mixture is reduced by removing a predetermined amount of at least one component by evaporation at a predetermined temperature and pressure thus producing a concentrated fourth liquid reaction mixture;

wherein the carbonylation catalyst composition contained in the concentrated fourth liquid reaction mixture is more active, than the carbonylation catalyst composition contained in said first liquid reaction mixture, at carbonylating an aromatic hydroxy compound in a subsequent oxidative carbonylation reaction.

86. A method for reactivating a deactivated catalyst composition used in an oxidative carbonylation reaction of phenol to produce diphenyl carbonate using carbon monoxide and oxygen, said catalyst composition comprising a palladium source, a lead source, a copper source, sodium bromide and a polyether solvent, contained in a first liquid reaction mixture further comprising phenol, diphenyl carbonate, and water, said method comprising the following steps:

a first addition step, in which an aqueous solution comprising hydrobromic acid is added to said first liquid reaction mixture, forming a biphasic second liquid reaction mixture composed of an organic layer and an aqueous layer;

a mixing step, whereby the biphasic second liquid reaction mixture is effectively agitated for a predetermined amount of time, followed by a settling stage in order to re-partition the mixture into the organic layer and the aqueous layer;

a first separation step, in which the aqueous layer of said biphasic second liquid reaction mixture is separated from said second liquid reaction mixture, to produce an aqueous third liquid reaction mixture; an optional second separation step, in which any precipitate which was present in the denser phase of the second liquid reaction mixture is separated from the denser phase obtained after the first separation step;

an optional second addition step, in which any metal containing precipitate which was separated during the second separation step, is added to the third liquid reaction mixture to produce a fourth liquid reaction mixture; and an evaporation step, wherein the volume of said fourth liquid reaction mixture is reduced by removing a predetermined amount of at least one component by evaporation at a predetermined temperature and pressure thus producing a concentrated fourth liquid reaction mixture;

wherein the carbonylation catalyst composition contained in the concentrated fourth liquid reaction mixture is more active, than the carbonylation catalyst composition contained in said first liquid reaction mixture, at carbonylating an aromatic hydroxy compound in a subsequent oxidative carbonylation reaction.

87. A method for reactivating a deactivated catalyst composition used in an oxidative carbonylation reaction of phenol to produce diphenyl carbonate using carbon monoxide and oxygen, said catalyst composition comprising a palladium source, a lead source, a titanium source, sodium bromide and a polyether solvent, contained in a first liquid reaction mixture further comprising phenol, diphenyl carbonate, and water, said method comprising the following steps:

a first addition step, in which an aqueous solution comprising hydrobromic acid is added to said first liquid reaction mixture, forming a biphasic second liquid reaction mixture composed of an organic layer and an aqueous layer;

a mixing step, whereby the biphasic second liquid reaction mixture is effectively agitated for a predetermined amount of time, followed by a settling stage in order to re-partition the mixture into the organic layer and the aqueous layer;

a first separation step, in which the aqueous layer of said biphasic second liquid reaction mixture is separated from said second liquid reaction mixture, to produce an aqueous third liquid reaction mixture;

an optional second separation step, in which any precipitate which was present in the denser phase of the second liquid reaction mixture is separated from the denser phase obtained after the first separation step;

an optional second addition step, in which any metal containing precipitate which was separated during the second separation step, is added to the third liquid reaction mixture to produce a fourth liquid reaction mixture; and an evaporation step, wherein the volume of said fourth liquid reaction mixture is reduced by removing a predetermined amount of at least one component by evaporation at a predetermined temperature and pressure thus producing a concentrated fourth liquid reaction mixture;

wherein the carbonylation catalyst composition contained in the concentrated fourth liquid reaction mixture is more active, than the carbonylation catalyst composition contained in said first liquid reaction mixture, at carbonylating an aromatic hydroxy compound in a subsequent oxidative carbonylation reaction.

88. A method for reactivating a deactivated catalyst composition used in an oxidative carbonylation reaction of phenol to produce diphenyl carbonate using carbon monoxide and oxygen, said catalyst composition comprising a palladium source, a lead source, sodium bromide and a polyether solvent, contained in a first liquid reaction mixture further comprising phenol, diphenyl carbonate, and water, said method comprising the following steps:

an optional first evaporation step, wherein the volume of the first liquid reaction mixture is reduced by removing a predetermined amount of at least one component by evaporation at a predetermined temperature and pressure to produce a concentrated first liquid reaction mixture;

a first addition step, in which an aqueous solution comprising hydrobromic acid is added to said first liquid reaction mixture, forming a biphasic second liquid reaction mixture composed of an organic layer and an aqueous layer;

a mixing step, whereby the biphasic second liquid reaction mixture is effectively agitated for a predetermined amount of time, followed by a settling stage in order to re-partition the mixture into the organic layer and the aqueous layer;

a first separation step, in which the organic layer of said second liquid reaction mixture, is separated from said second liquid reaction mixture after a predetermined amount of time, to produce an aqueous third liquid reaction mixture;

an optional second separation step, in which any precipitate which was present in the denser phase of the second liquid reaction mixture is separated from the denser phase obtained after the first separation step;

an optional second evaporation step, wherein the volume of said aqueous third liquid reaction mixture is reduced by removing a predetermined amount of at least one component by evaporation at a predetermined temperature and pressure to produce a concentrated third liquid reaction mixture;

a second addition step, wherein a solution comprising at least one member selected from the group consisting of an activating solvent, an aromatic hydroxy compound, an aromatic carbonate, and any mixtures thereof is added to the third liquid reaction mixture, forming a fourth liquid reaction mixture;

a third evaporation step, wherein the volume of the fourth liquid reaction mixture is reduced by removing a predetermined amount of at least one component by evaporation at a predetermined temperature and pressure to produce a concentrated fourth liquid reaction mixture;

a third separation step, in which any components that precipitate from the concentrated fourth liquid reaction mixture after a predetermined amount of time are separated from the concentrated fourth liquid reaction mixture, therein producing a fifth liquid reaction mixture;

an third addition step, wherein at least one member selected from the group consisting of an aromatic hydroxy compound, an organic ligand source, an aromatic carbonate, a salt source, an activating solvent, a base source, and any mixtures thereof, is added to the fifth liquid reaction mixture to produce a sixth liquid reaction mixture; and an optional fourth addition step, wherein any metal containing precipitate which was separated during the second separation step is added to the sixth liquid reaction mixture, therein producing an seventh liquid reaction mixture;

wherein the carbonylation catalyst composition contained in said seventh liquid reaction mixture is more active than the carbonylation catalyst composition contained is said first liquid reaction mixture at carbonylating an aromatic hydroxy compound in a subsequent oxidative carbonylation reaction.

89. A method for reactivating a deactivated catalyst composition used in an oxidative carbonylation reaction of phenol to produce diphenyl carbonate using carbon monoxide and oxygen, said catalyst composition comprising a palladium source, a lead source, a copper source, sodium bromide, and a polyether solvent, contained in a first liquid reaction mixture further comprising phenol, diphenyl carbonate, and water, said method comprising the following steps:

an optional first evaporation step, wherein the volume of the first liquid reaction mixture is reduced by removing a predetermined amount of at least one component by evaporation at a predetermined temperature and pressure to produce a concentrated first liquid reaction mixture;

a first addition step, in which an aqueous solution comprising hydrobromic acid is added to said first liquid reaction mixture, forming a biphasic second liquid reaction mixture composed of an organic layer and an aqueous layer;

a mixing step, whereby the biphasic second liquid reaction mixture is effectively agitated for a predetermined amount of time, followed by a settling stage in order to re-partition the mixture into the organic layer and the aqueous layer;

a first separation step, in which the organic layer of said second liquid reaction mixture, is separated from said second liquid reaction mixture after a predetermined amount of time, to produce an aqueous third liquid reaction mixture;

an optional second separation step, in which any precipitate which was present in the denser phase of the second liquid reaction mixture is separated from the denser phase obtained after the first separation step;

an optional second evaporation step, wherein the volume of said aqueous third liquid reaction mixture is reduced by removing a predetermined amount of at least one component by evaporation at a predetermined temperature and pressure to produce a concentrated third liquid reaction mixture;

a second addition step, wherein a solution comprising at least one member selected from the group consisting of an activating solvent, an aromatic hydroxy compound, an aromatic carbonate, and any mixtures thereof is added to the third liquid reaction mixture, forming a fourth liquid reaction mixture;

a third evaporation step, wherein the volume of the fourth liquid reaction mixture is reduced by removing a predetermined amount of at least one component by evaporation at a predetermined temperature and pressure to produce a concentrated fourth liquid reaction mixture;

a third separation step, in which any components that precipitate from the concentrated fourth liquid reaction mixture after a predetermined amount of time are separated from the concentrated fourth liquid reaction mixture, therein producing a fifth liquid reaction mixture;

an third addition step, wherein at least one member selected from the group consisting of an aromatic hydroxy compound, an organic ligand source, an aromatic carbonate, a salt source, an activating solvent, a base source, and any mixtures thereof, is added to the fifth liquid reaction mixture to produce a sixth liquid reaction mixture; and an optional fourth addition step, wherein any metal containing precipitate which was separated during the second separation step is added to the sixth liquid reaction mixture, therein producing an seventh liquid reaction mixture;

wherein the carbonylation catalyst composition contained in said seventh liquid reaction mixture is more active than the carbonylation catalyst composition contained is said first liquid reaction mixture at carbonylating an aromatic hydroxy compound in a subsequent oxidative carbonylation reaction.

90. A method for reactivating a deactivated catalyst composition used in an oxidative carbonylation reaction of phenol to produce diphenyl carbonate using carbon monoxide and oxygen, said catalyst composition comprising a palladium source, a lead source, a titanium source, sodium bromide, and a polyether solvent, contained in a first liquid reaction mixture further comprising phenol, diphenyl carbonate, and water, said method comprising the following steps:

an optional first evaporation step, wherein the volume of the first liquid reaction mixture is reduced by removing a predetermined amount of at least one component by evaporation at a predetermined temperature and pressure to produce a concentrated first liquid reaction mixture;

a first addition step, in which an aqueous solution comprising hydrobromic acid is added to said first liquid reaction mixture, forming a biphasic second liquid reaction mixture composed of an organic layer and an aqueous layer;

a mixing step, whereby the biphasic second liquid reaction mixture is effectively agitated for a predetermined amount of time, followed by a settling stage in order to re-partition the mixture into the organic layer and the aqueous layer;

a first separation step, in which the organic layer of said second liquid reaction mixture, is separated from said second liquid reaction mixture after a predetermined amount of time, to produce an aqueous third liquid reaction mixture;

an optional second separation step, in which any precipitate which was present in the denser phase of the second liquid reaction mixture is separated from the denser phase obtained after the first separation step;

an optional second evaporation step, wherein the volume of said aqueous third liquid reaction mixture is reduced by removing a predetermined amount of at least one component by evaporation at a predetermined temperature and pressure to produce a concentrated third liquid reaction mixture;

a second addition step, wherein a solution comprising at least one member selected from the group consisting of an activating solvent, an aromatic hydroxy compound, an aromatic carbonate, and any mixtures thereof is added to the third liquid reaction mixture, forming a fourth liquid reaction mixture;

a third evaporation step, wherein the volume of the fourth liquid reaction mixture is reduced by removing a predetermined amount of at least one component by evaporation at a predetermined temperature and pressure to produce a concentrated fourth liquid reaction mixture;

a third separation step, in which any components that precipitate from the concentrated fourth liquid reaction mixture after a predetermined amount of time are separated from the concentrated fourth liquid reaction mixture, therein producing a fifth liquid reaction mixture;

an third addition step, wherein at least one member selected from the group consisting of an aromatic hydroxy compound, an organic ligand source, an aromatic carbonate, a salt source, an activating solvent, a base source, and any mixtures thereof, is added to the fifth liquid reaction mixture to produce a sixth liquid reaction mixture; and an optional fourth addition step, wherein any metal containing precipitate which was separated during the second separation step is added to the sixth liquid reaction mixture, therein producing an seventh liquid reaction mixture;

wherein the carbonylation catalyst composition contained in said seventh liquid reaction mixture is more active than the carbonylation catalyst composition contained is said first liquid reaction mixture at carbonylating an aromatic hydroxy compound in a subsequent oxidative carbonylation reaction.

91. A method for reactivating a deactivated carbonylation catalyst composition comprising a Group 8, 9 or 10 catalyst source, and a Group 7 metal inorganic co-catalyst, which is present in a first liquid reaction mixture, said method comprising the following steps:

an addition step, in which an aqueous solution comprising at least one protic acid source is added to said first liquid reaction mixture, forming a biphasic second liquid reaction mixture composed of an organic layer and an aqueous layer;

a mixing step, whereby the biphasic second liquid reaction mixture is effectively agitated for a predetermined amount of time, followed by a settling stage in order to repartition the second liquid reaction mixture into the organic layer and the aqueous layer;

a separation step, in which the organic layer of said biphasic second liquid reaction mixture is separated from said second liquid reaction mixture, to produce an aqueous third liquid reaction mixture; and an evaporation step, wherein the volume of said aqueous third liquid reaction mixture is reduced by removing a predetermined amount of at least one component by evaporation at a predetermined temperature and pressure thus producing a concentrated third liquid reaction mixture;

wherein the carbonylation catalyst composition contained in the concentrated third liquid reaction mixture is more active, than the carbonylation catalyst composition contained in said first liquid reaction mixture, at carbonylating an aromatic hydroxy compound in a subsequent oxidative carbonylation reaction.

92. The method of claim 91, wherein the Group 8, 9 or 10 metal source is a palladium source.

93. The method of claim 92, wherein the Group 7 metal source is a manganese source.

94. The method of claim 93, wherein the palladium source is present in an amount which is between about 1 ppm and 10000 ppm, and the manganese source is present in an amount which is between about 1 equivalent and about 1000 equivalents versus the amount of palladium present.

95. The method of claim 94, wherein the carbonylation catalyst composition further comprises a salt source.

96. The method of claim 95, wherein the salt source is at least one member selected from the group consisting of an alkali halide, an alkaline-earth halide, a guanidinium halide, an ammonium halide, a phosphonium halide, a sulfonium halide, a carboxylate, an acetate, and a nitrate.

97. The method of claim 95, wherein the salt source is at least one member selected from the group consisting of lithium bromide, sodium bromide, potassium bromide, calcium bromide, magnesium bromide, tetrabutylammonium bromide, tetraethylammonium bromide, tetramethylammonium bromide, hexaethylguanidinium bromide, lithium chloride, sodium chloride, potassium chloride, calcium chloride, magnesium chloride, tetrabutylammonium chloride, tetraethylammonium chloride, tetramethylammonium chloride, hexaethylguanidinium chloride, sodium acetate, and sodium nitrate.

98. The method of claim 95, wherein the salt source is present in an amount which is between about 1 equivalent and about 100000 equivalents versus the amount of Group 8, 9 or 10 metal source present.

99. The method of claim 91, wherein the carbonylation catalyst composition further comprises at least one activating solvent.

100. The method of claim 99, wherein the activating solvent is one member selected from the group consisting of a polyether, a nitrile, and mixtures thereof.

101. The method of claim 100, wherein the activating solvent is present in an amount which between about 0.1 weight % and about 50 weight % based on the total weight of the first liquid reaction mixture.

102. The method of claim 91, wherein the carbonylation catalyst composition further comprises at least one base source.

103. The method of claim 102, wherein the base source is at least one member selected from the group consisting of a basic oxide, a hydroxide, a mono-alkoxide, a poly-alkoxide, a monocyclic aryloxide, a polycyclic aryloxide, and a tertiary amine.

104. The method of claim 102, wherein the base source is at least one member selected from the group consisting of sodium hydroxide, lithium hydroxide, potassium hydroxide, tetramethylammonium hydroxide, tetraethylammonium hydroxide, methyltributylammonium hydroxide, tetrabutylammonium hydroxide, sodium phenoxide, lithium phenoxide, potassium phenoxide, tetramethylammonium phenoxide, tetraethylammonium phenoxide, methyltributylammonium phenoxide, tetrabutylammonium phenoxide, triethyl amine, tributyl amine, and any mixtures thereof.

105. The method of claim 102, wherein the base source is present in an amount which is between about 1 equivalent and about 10000 equivalents versus the amount of Group 8, 9 or 10 metal source present.

106. The method of claim 91, wherein the first liquid reaction mixture comprises at least one member selected from the group consisting of an aromatic carbonate, an aromatic hydroxy compound, a poly-aromatic hydroxy compound, a halogenated aromatic hydroxy compound, water, an aryl ether, and any mixtures thereof.

107. The method of claim 91, wherein the protic acid source is at least one member selected from the group consisting of hydrobromic acid, hydrochloric acid, sulfuric acid, nitric acid, acetic acid, and any mixtures thereof.

108. The method of claim 107, wherein the amount of protic acid source present in the aqueous solution is between about 1 weight % and about 48 weight % based on the total weight of the aqueous solution.

109. The method of claim 108, wherein the addition of the aqueous solution is made by using at least one aliquot of an aqueous solution, wherein the amount of protic acid source present in each individual aliquot is different, and wherein the resulting second liquid reaction mixture contains two phases after all the aliquots have been added, and wherein the total volume of the aqueous solution added to the first liquid reaction mixture is between about 1% and about 200% of the volume of the first liquid reaction mixture.

110. The method of claim 109, wherein the extraction time after the addition of each aliquot is between about 0.1 minutes and 120 minutes, and the temperature of the liquid reaction mixture after the addition of each aliquot is between about 60° C. and about 140° C.

111. The method of claim 91, wherein the addition of the aqueous solution to the first liquid reaction mixture, the mixing step, and the separation step where the organic layer is separated from the second liquid reaction mixture, are performed by using an extraction column, or a mixer followed by an extraction column.

112. The method of claim 91, wherein the addition of the aqueous solution to the first liquid reaction mixture, the mixing step, and the separation step where the organic layer is separated from the second liquid reaction mixture, are performed using a mixer-settler vessel.

113. The method of claim 91, wherein the separation of the aqueous layer from the third liquid reaction mixture is by decanting.

114. The method of claim 91, wherein the volume of the third liquid reaction mixture is reduced by up to about 95% by evaporation in the evaporation step.

115. The method of claim 91, wherein the temperature of third liquid reaction mixture during the evaporation step is between about 25° C. and about 220° C., and the pressure during the evaporation step is between about $1.3 \times 10^{-4}$ MPa and about 10 MPa.

* * * * *